(12) United States Patent
Czimmek et al.

(10) Patent No.: US 6,359,435 B1
(45) Date of Patent: Mar. 19, 2002

(54) METHOD FOR DETERMINING MAGNETIC CHARACTERISTICS OF AN ELECTRONICALLY CONTROLLED SOLENOID

(75) Inventors: Perry Robert Czimmek, Williamsburg; Danny Orlen Wright, Cobb's Creek, both of VA (US)

(73) Assignee: Siemens Automotive Corporation, Auburn Hills, MI (US)

( * ) Notice: Subject to any disclaimer, the term of this patent is extended or adjusted under 35 U.S.C. 154(b) by 0 days.

(21) Appl. No.: 09/276,223

(22) Filed: Mar. 25, 1999

(51) Int. Cl.$^7$ .......................... G01R 33/12; G01N 27/72; F01L 9/04
(52) U.S. Cl. .................. 324/234; 324/223; 324/238; 324/415; 324/546; 123/90.11; 361/154
(58) Field of Search ................. 324/202, 222, 324/223, 234, 238, 207.15, 207.16, 207.17, 415, 418, 545, 546, 654, 263; 361/154, 160; 340/644; 123/90.11

(56) References Cited

U.S. PATENT DOCUMENTS

| | | | |
|---|---|---|---|
| 3,671,814 A | 6/1972 | Dick | 317/123 |
| 4,328,526 A | 5/1982 | Dilger et al. | 361/154 |
| 4,368,501 A | 1/1983 | Gingrich | 361/152 |
| 4,515,343 A | 5/1985 | Pischinger et al. | 251/48 |
| 4,593,658 A | 6/1986 | Moloney | 123/90 |
| 4,823,825 A | 4/1989 | Buchl | 137/1 |
| 4,870,364 A * | 9/1989 | Trox et al. | 324/418 |
| 4,941,348 A * | 7/1990 | Hock | 324/654 X |
| 4,955,334 A | 9/1990 | Kawamura | 123/90 |
| 4,957,074 A | 9/1990 | Weissler et al. | 123/90 |
| 4,990,854 A * | 2/1991 | Friz | 324/418 |
| 5,000,389 A | 4/1991 | Kawamura | 251/129.1 |
| 5,442,515 A | 8/1995 | Wallaert | 361/187 |
| 5,481,187 A * | 1/1996 | Marcott et al. | 324/207.16 |
| 5,523,684 A | 6/1996 | Zimmermann | 324/207.22 |
| 5,650,909 A | 7/1997 | Remele et al. | 361/154 |
| 5,673,165 A | 9/1997 | Kuhn et al. | 361/154 |
| 5,691,680 A | 11/1997 | Schrey et al. | 335/256 |
| 5,701,870 A | 12/1997 | Gottshall et al. | 123/490 |
| 5,708,355 A | 1/1998 | Schrey | 323/282 |
| 5,711,259 A | 1/1998 | Pischinger et al. | 123/90 |
| 5,729,119 A | 3/1998 | Barbour | 323/222 |
| 5,742,467 A | 4/1998 | Schmitz | 361/154 |
| 5,748,433 A | 5/1998 | Schrey et al. | 361/210 |
| 5,769,043 A | 6/1998 | Nitkiewicz | 123/90.11 |
| 5,775,276 A | 7/1998 | Yanai et al. | 123/90.11 |
| 5,785,016 A | 7/1998 | Enderle et al. | 123/90.11 |
| 5,797,360 A | 8/1998 | Pischinger et al. | 123/90.11 |
| 5,868,108 A | 2/1999 | Schmitz et al. | 123/90.11 |
| 5,887,553 A | 3/1999 | Ballmann et al. | 123/90.11 |
| 5,991,143 A * | 11/1999 | Wright et al. | |
| 6,176,207 B1 | 1/2001 | Wright et al. | 123/90.11 |

* cited by examiner

Primary Examiner—Gerard R. Strecker (57) ABSTRACT

A method is provided for determining magnetic characteristics of an electrically controlled solenoid. The method includes providing an electronically controlled solenoid having an armature, a stator and a coil operatively associated with the stator. The armature, stator and coil define a magnetic circuit. The armature is spaced from the stator to define an air gap between the armature and the stator. Current to the coil is ramped in a generally linear manner over a period of time to define a known current curve. A resulting rate of change of flux in the magnetic circuit is observed and recorded at certain points along the current curve. In accordance with another aspect of the invention, flux in the magnetic circuit is ramped in a generally linear manner over a period of time to define a known flux curve. A resulting current in the coil is observed and recorded at certain points along the flux curve. With the method, a magnetization curve may be developed wherein flux may be determined at any point along a curve for a given amount of current in a solenoid.

24 Claims, 8 Drawing Sheets

METHOD FOR DETERMINING MAGNETIC CHARACTERISTICS OF AN ELECTRONICALLY CONTROLLED SOLENOID

FIELD OF THE INVENTION

This invention relates to electronically controlled solenoids and more particularly to a method of determining magnetic characteristics of a solenoid in its finished product state.

BACKGROUND OF THE INVENTION

A conventional electromagnetic actuator for opening and closing a valve of an internal combustion engine generally includes a solenoid which, when energized, produces an electromagnetic force on an armature. The armature is biased by a return spring and the armature is coupled with a cylinder valve of the engine. The armature is held by the electromagnet in one operating position against a stator core of the actuator and, by deenergizing the electromagnet, the armature may move towards and into another operating position by the return spring.

Conventional high speed electronic solenoids of the fuel injector type include an armature to control movement of an injector valve.

In solenoids of either an electromagnetic actuator or a fuel injector type, it may be desirable, for control or other purposes, to know certain magnetic characteristics of the solenoid. For example, it may be desirable to know when the magnetic circuit approaches saturation, what current levels are expected in order to deliver a desired flux, where significant non-linearities arise along a magnetization curve, how the magnetization curve varies over the operation, life or temperature of the solenoid, or how the current varies due to demands of building flux.

A magnetization curve of a solenoid generally comprises two parameters: magnetic flux density and magnetomotive force. The magnetomotive force is that which tends to produce a magnetic field. In a solenoid, this force is most commonly produced by a current flowing through a coil of wire and the magnitude of the force is proportional to the current and the number of turns of the coil. For simplicity, flux and current may be the two parameters of a magnetization curve.

Since the purpose of a solenoid is to produce a force to perform work and force is the result of a magnetic field (flux), and the magnetic field is the result of electrical current applied to the solenoid, it would seem reasonable that if the current applied was known, the force the solenoid is producing would be known. However, the force the solenoid is producing cannot be obtained by simply measuring current. Due to the variations of magnetic characteristics of the ferromagnetic circuit, the amount of flux and therefore force generated for a given amount of current varies.

Conventionally, the magnetization curve has been assumed, within an error, based on data provided from the manufacturer of the raw magnetic alloy used in the magnetic circuit. Thus, the magnetization curve has classically remained an engineering design variable.

Accordingly, there is a need to determine magnetic characteristics of a solenoid electronically and develop a magnetization curve in a simple and real time output, and to use the magnetization curve in the electronic control of a solenoid.

SUMMARY OF THE INVENTION

An object of the present invention is to fulfill the need referred to above. In accordance with the principles of the present invention, this objective is obtained by providing a method of determining magnetic characteristics of an electrically controlled solenoid. The method includes providing an electronically controlled solenoid having an armature, a stator and a coil operatively associated with the stator. The armature, stator and coil define a magnetic circuit. The armature is spaced from the stator to define an air gap between the armature and the stator. Current to the coil is ramped in a generally linear manner over a period of time to define a known current curve. A resulting rate of change of flux in the magnetic circuit is observed and recorded at certain points along the current curve.

In accordance with another aspect of the invention, flux in the magnetic circuit is ramped in a generally linear manner over a period of time to define a known flux curve. A resulting current in the coil is observed and recorded at certain points along the flux curve.

With the above method, a magnetization curve may be developed wherein flux may be determined at any point along a curve for a given amount of current in a solenoid.

Other objects, features and characteristic of the present invention, as well as the methods of operation and the functions of the related elements of the structure, the combination of parts and economics of manufacture will become more apparent upon consideration of the following detailed description and appended claims with reference to the accompanying drawings, all of which form a part of this specification.

DETAILED DESCRIPTION OF THE INVENTION

Figure 1:
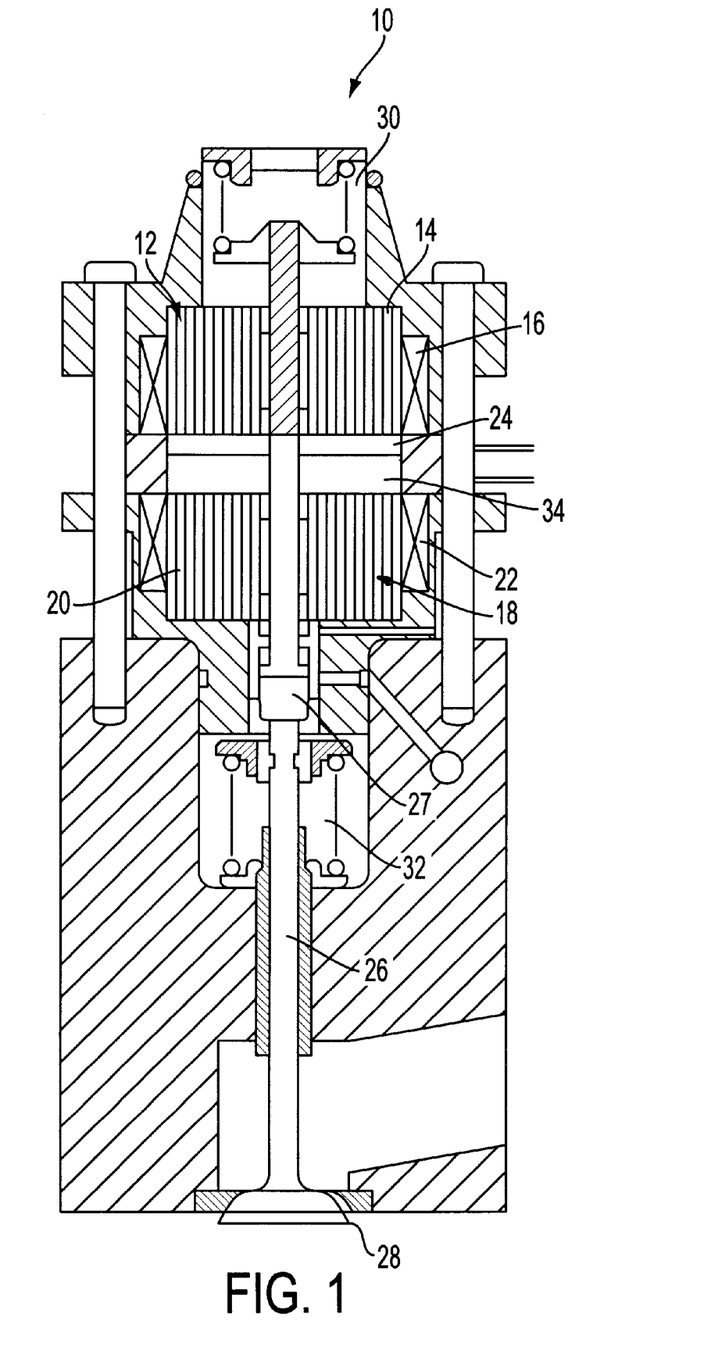
FIG. 1 is a cross-sectional view of a solenoid device, in particular an electromagnetic actuator, provided in accordance with the principles of the present invention, shown coupled with a gas exchange valve of an engine.

Referring to FIG. 1, an electromagnetic actuator or solenoid is shown, generally indicated 10, which represents a solenoid of which magnetic characteristics are determined in accordance with the principles of the present invention. Although an electromagnetic actuator for use in electronic valve timing is shown to represent a solenoid for the purposes of describing the invention, the invention is not limited to an actuator. The invention relates to any electronically controlled solenoids.

The electromagnetic solenoid 10 includes a first electromagnet, generally indicated at 12, which includes a stator core 14 and a solenoid coil 16 associated with the stator core 14. A second electromagnet, generally indicated at 18, is disposed generally in opposing relation to the first electromagnet 12. The second electromagnet 18 includes a stator core 20 and a solenoid coil 22 associated with the stator core 20. The electromagnetic actuator 10 includes a ferromagnetic armature 24 which is attached to a stem 26 of a fluid exchange valve 28 through a hydraulic valve adjuster 27. The armature 24 is disposed generally between the electromagnets 12 and 18 so as to be acted upon by the an electromagnetic force created by the electromagnets. In a deenergized state of the electromagnets 12 and 18, the armature 24 is maintained in a position of rest generally between the two electromagnets 12 and 18 by opposing working return springs 30 and 32. In a valve closed position (FIG. 1), the armature 24 engages the stator core 14 of the first electromagnet 12.

Each stator core and associated coil together With the armature 24 define a magnetic circuit of the solenoid 10. Further, as shown in FIG. 1, an air gap 34 is provided between the armature 24 and the second electromagnet 18. It can be appreciated that an air gap is defined between the armature 24 and the upper electromagnet 12 at certain times during the oscillation of the armature 24. The air gap 34 is the magnetic discontinuity in a ferromagnetic circuit which increases the reluctance (resistance to flux) of the circuit.

While keeping the armature 24 stationary, solenoid coil 22 may be energized causing a flux linkage to build up to some flux density. The resulting flux at the air gap 34 and the concentration of flux through and around the lower reluctance armature 24 results in a distorted flux field and therefore a net force on the armature 24 in the direction of decreasing reluctance (smaller gap).

U.S. patent application Ser. No. 09/025,986, now U.S. Pat. No. 6,176,207, entitled "Electronically Controlling the Landing of an Armature in an Electromagnetic Actuator", the contents of which are hereby incorporated into the present specification by reference, discloses using a flux sensor to sense a rate of change of magnetic flux in an electromagnetic actuator. The rate of change of flux sensed is used as a feedback variable to control a landing velocity of an armature of the actuator. U.S. patent application Ser. No. 09/122,042, now U.S. Pat. No. 5,991,143, entitled "A Method For Controlling Velocity Of An Armature of An electromagnetic Actuator", the contents of which are hereby incorporated into the present specification by reference, discloses feedback control based on a rate of change of magnetic flux without the need for a flux sensor.

The invention utilizes closed loop flux control to determine magnetic characteristic of an electronically controlled solenoid.

Figure 2:
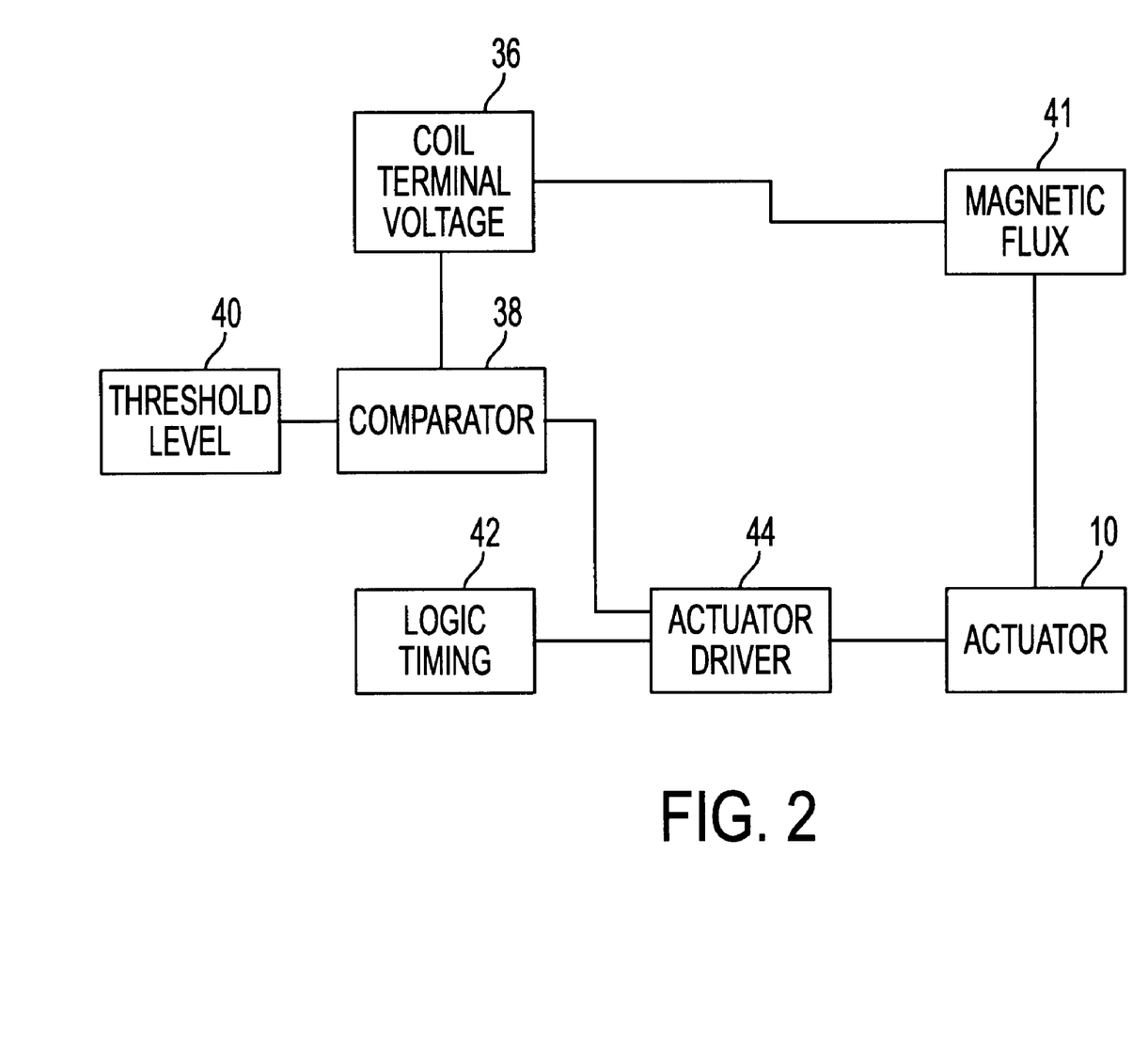
FIG. 2 is a block diagram of circuit structure of the solenoid device of FIG. 1.

With reference to FIG. 2, a block diagram of a circuit structure according to one embodiment of the present invention is shown which incorporates closed loop feedback of magnetic flux. The circuit structure is based on controlling the armature velocity near landing by regulating a rate of change of magnetic flux in the armature/stator magnetic circuit by measuring the terminal voltage of the coil 22. In the circuit of the FIG. 2, a terminal voltage 36 of the coil 22 is applied to a comparator 38. A threshold level 40 is also applied to the comparator 38. The output of the comparator 38 is "logically added" with a logic timing component 42 and is supplied to an actuator driver 44 to drive the actuator 10. Once the actuator driver 44 is energized, the solenoid coil 22 is energized.

The measured coil terminal voltage 36 is compared to the threshold level 40 and the threshold level 40 is used to control a catch current supplied to the solenoid coil 22 of the actuator 10 and thus control the magnetic flux 41.

Although measuring the coil terminal voltage directly is effective for controlling the landing of the armature 24 of the actuator 10, it is preferable to not physically measure the high common mode voltage typically present at each terminal of the coil 22. Thus, a parametrically determined mirror image of the coil terminal voltage and hence a mirror image of the rate of change of flux in the actuator's magnetic circuit may be provided by the circuit of the actuator 10 such that there is no need to physically touch the coil terminals to measure the coil terminal voltage.

Figure 3:
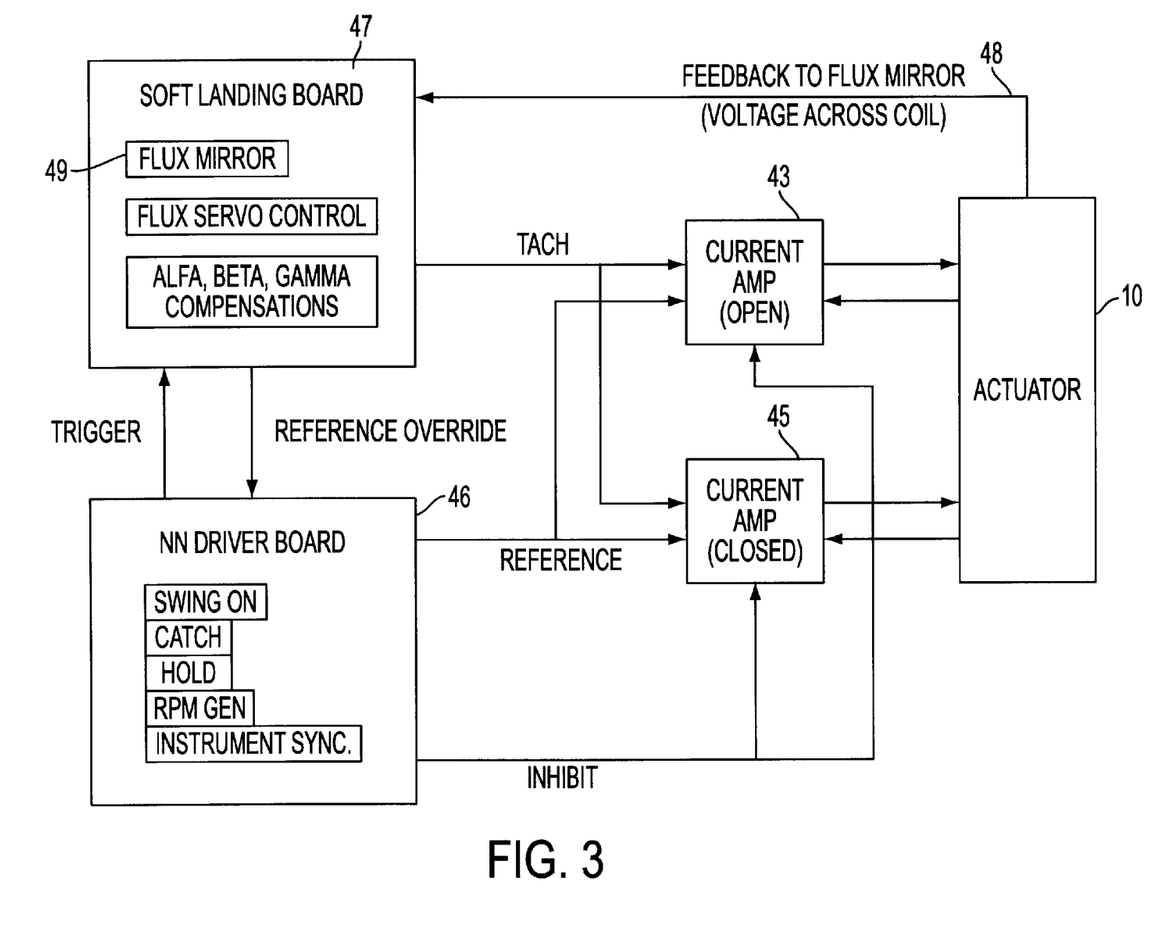
FIG. 3 is a block diagram of a second embodiment of circuit structure of the solenoid device of FIG. 1.

With reference to FIG. 3, a system block diagram for controlling the solenoid or actuator 10 is shown which uses a "flux mirror" circuit. The actuator 10 is electrically connected to an "open" current amp 43 and a "close" current amp 45. The current amps 43 and 45 are connected to a programmable current regulator or driver board 46. The programming for controlling current is performed by a soft landing circuit board 47 which commands and regulates the desired rates of change of magnetic flux required to control the magnetic force on the armature 24 of the actuator 10, and therefore, command the flux shape. Closed loop flux regulation is accomplished by feedback of the actuator coil voltage 48 to a flux mirror circuit 49 on the soft landing circuit board 47.

Figure 4:
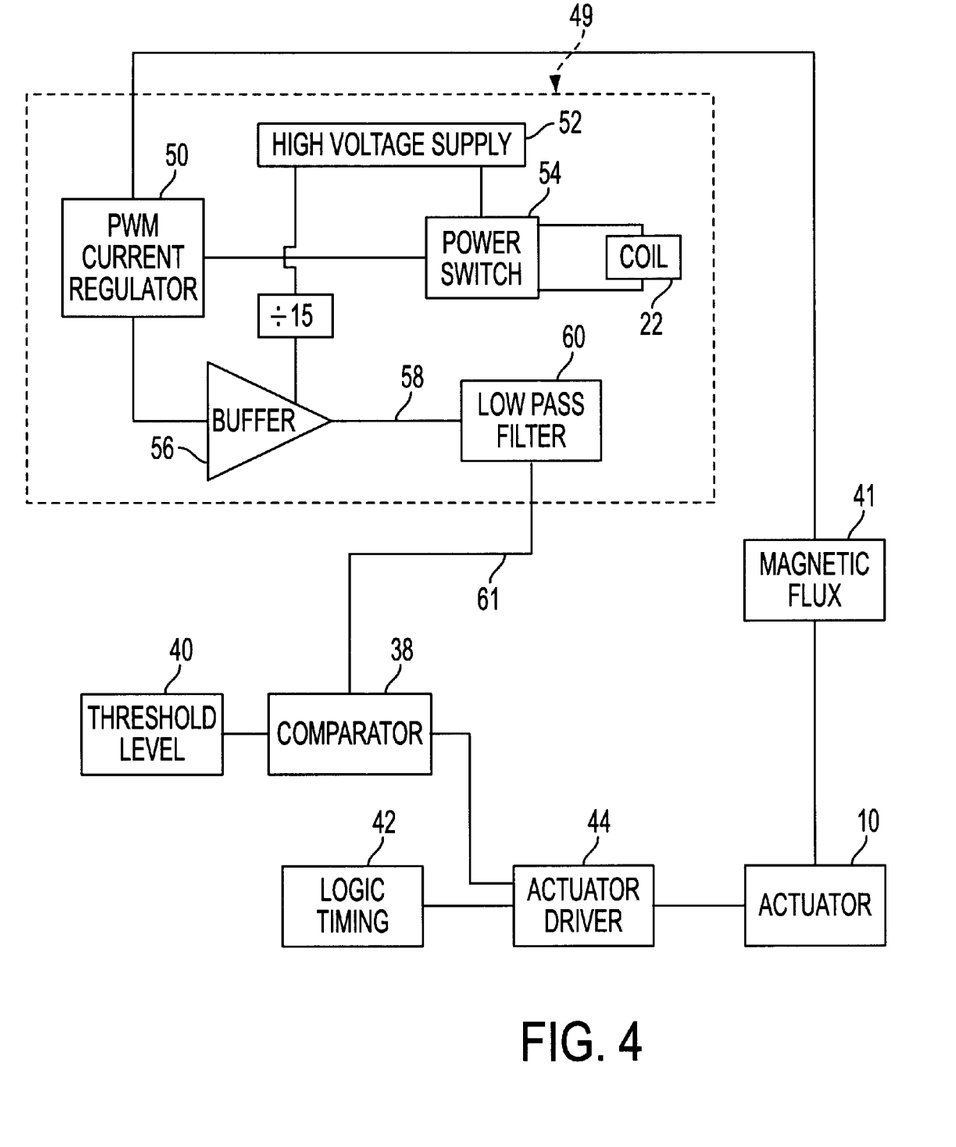
FIG. 4 is a block diagram showing a flux mirror circuit of the circuit structure of FIG. 3.

FIG. 4 shows the flux mirror circuit 49 block diagram of the actuator 10. The solenoid coil 22 of the actuator 10 is driven preferably by a PWM (switchmode) current regulator 50 which provides a pulse train to a high voltage power transistor stage (including a high operating voltage supply 52 and a power switch 54) which subsequently switches voltage pulses across the load of the coil 22. It can be appreciated that power can be regulated by other means, such as, for example, a voltage regulator or amplifier. The flux mirror addition to this conventional approach consists of routing the logic level PWM signal from the current regulator 50 through a buffer 56. The rail voltage of the buffer 56 is derived from a scaled-down replica of the system high voltage supply 52. Finally, the scaled and buffered pulse train 58 is smoothed by a low pass filter 60 and is applied to the comparator 38. The threshold level 40 is also applied to the comparator 38. The output of the comparator 38 is "logically added" with a logic timing component 42 and is supplied to the driver 44 to drive the actuator 10. Once the actuator driver 44 is energized, the solenoid coil 22 is energized. The smoothed pulse train 61 from the low pass filter 60 is compared to the threshold level 40 and the threshold level 40 is used to control a catch current supplied to the solenoid coil 22 of the actuator 10 and thus control the magnetic flux 41.

The time constant of the low pass filter 60 is selected to match the rate of armature motion in the actuator 10. The output from the low pass filter 60 is scaled-down from and mirrors the high operating voltage of the coil 22 and corresponds to the desired time rate of change of magnetic flux d(phi)/dt which is used as a feedback variable to control the landing velocity of the armature 24.

Figure 5:
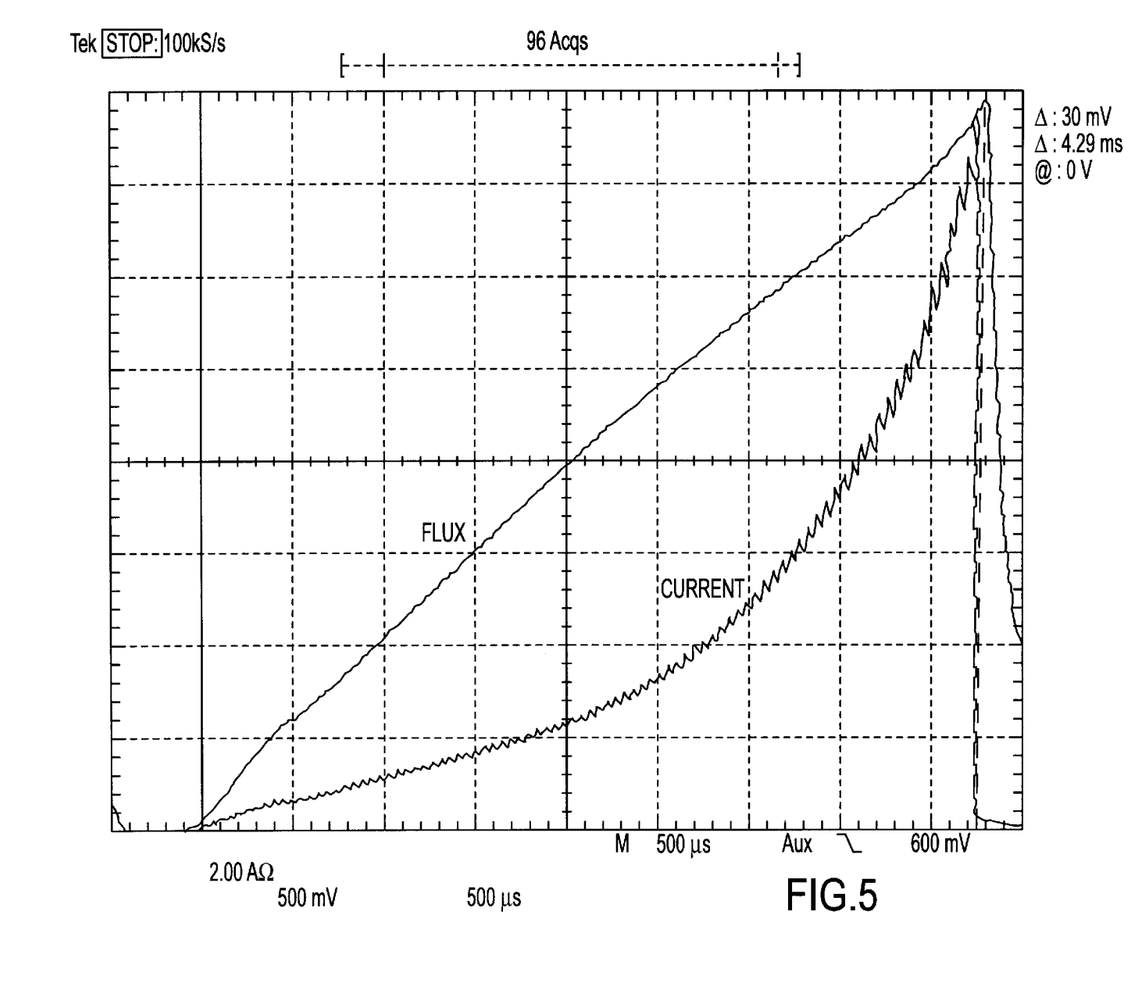
FIG. 5 is a graph of the invention showing ramped flux and responsive current of the solenoid device of FIG. 1 having an air gap of 200 microns.
Figure 6:
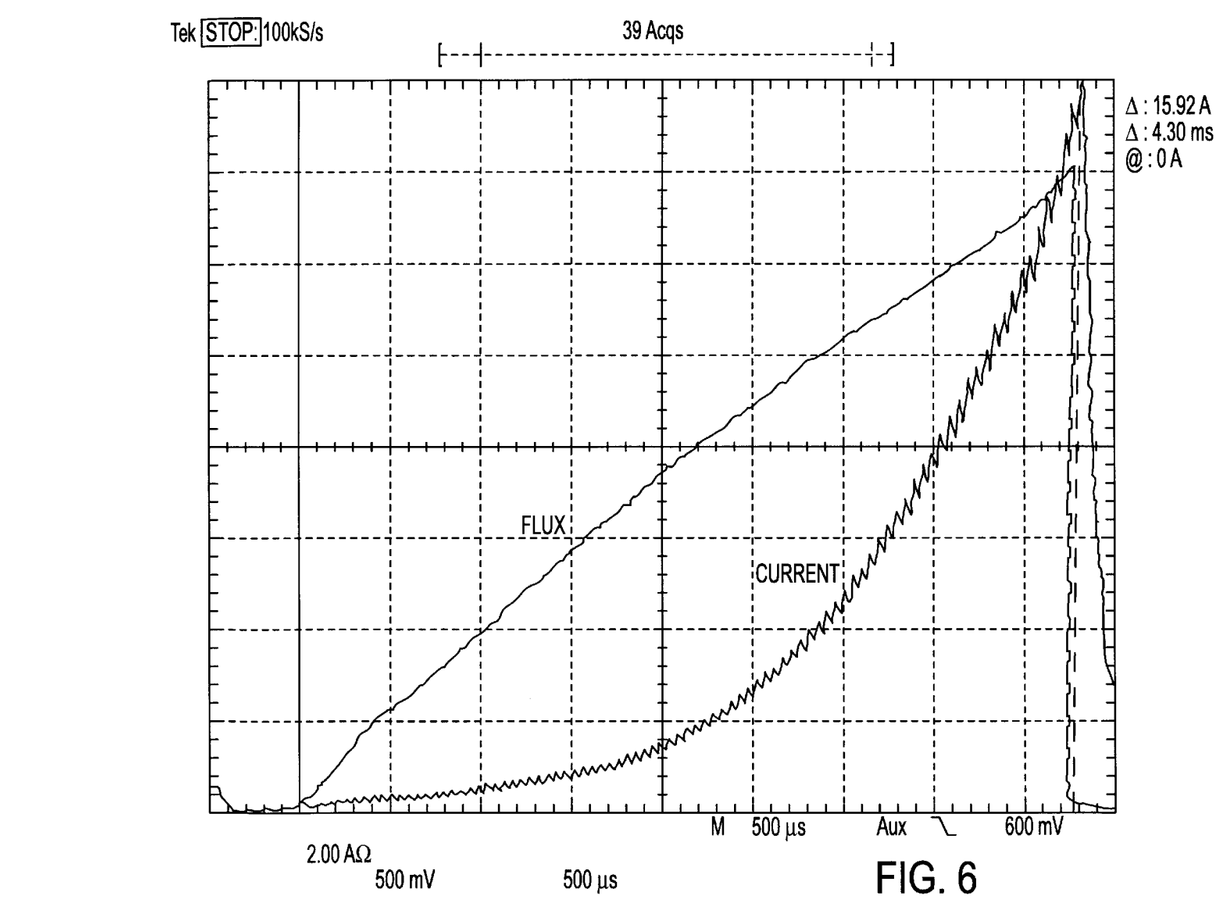
FIG. 6 is a graph of the invention showing ramped flux and responsive current of the solenoid device of FIG. 1 having an air gap of 20 microns.
Figure 7:
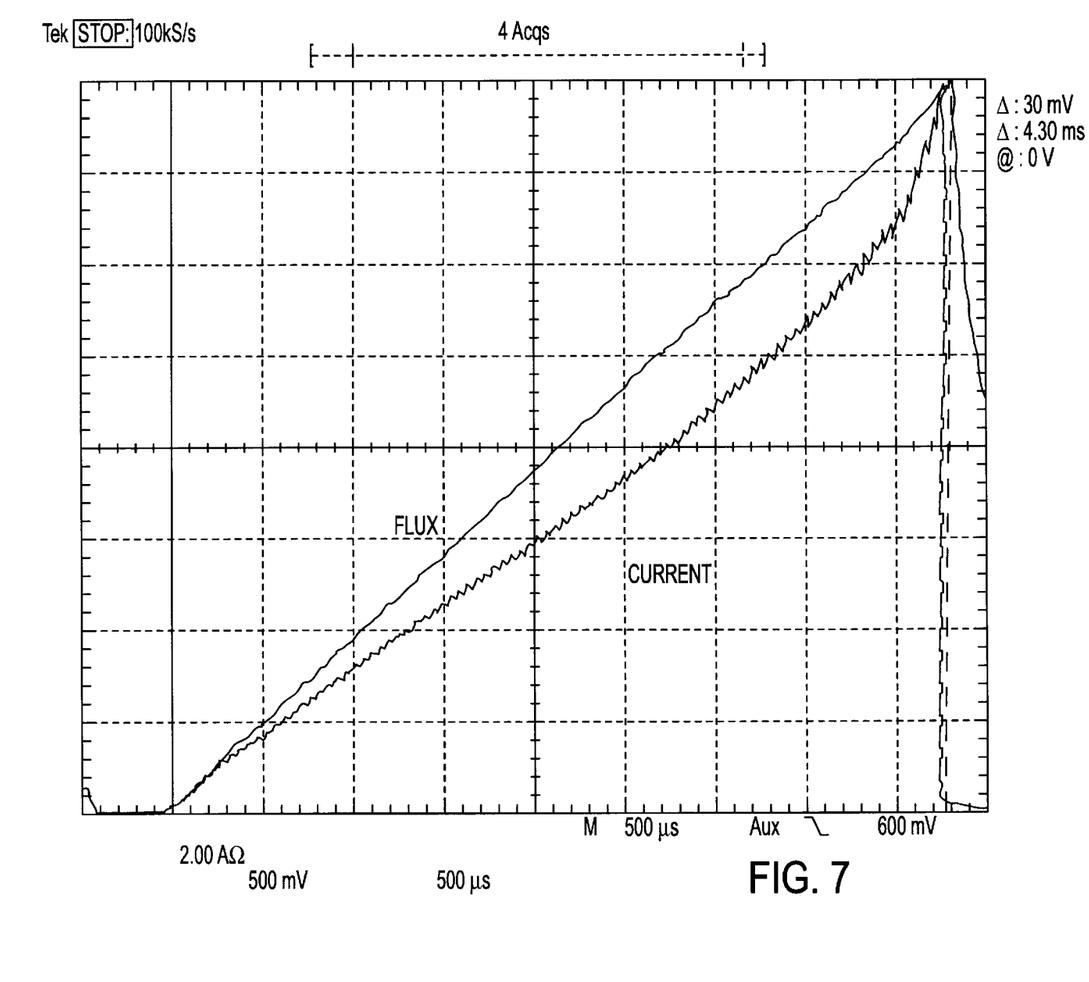
FIG. 7 is a graph of the invention showing ramped flux and responsive current of the solenoid device of FIG. 1 having an air gap of 2 mm.

In accordance with the invention, to determine magnetic characteristics of the solenoid 10, the armature 24 was in a static condition (the air gap 34 being fixed). The number of turns of the coil 22 was fixed at 200 turns and the parameters of flux and current were the remaining controlled or observed variables. With reference to FIGS. 5–7, one approach to determine magnetic characteristics of a solenoid is ramp flux in a generally linear manner to define a known flux curve and then to observe the resulting current in coil 22 along the flux curve. FIG. 5 shows a current curve resulting from ramped flux when the air gap 34 of the actuator 10 was set at 200 microns. FIG. 6 shows a current curve resulting from ramped flux when the air gap 34 of the actuator 10 was set at 20 microns. FIG. 7 shows a current curve resulting from ramped flux when the air gap 34 of the actuator 10 was set at 2 mm.

Another approach to determine magnetic characteristics of a solenoid is to ramp the current of coil 22 in a generally linear manner to define a known current curve and then to observe the resulting rate of change of magnetic flux in the magnetic circuit defined by the coil 22, stator 20 and armature 24. The rate of change of magnetic flux may then be integrated to determine flux.

The rate of change of flux may be determined and controlled by using a flux sensor such as a Hall effect sensor, or by measuring the terminal voltage of the coil 22, or by using a "flux mirror" circuit which mirrors the terminal voltage of the coil 22, as explained above.

In a solenoid operated device such as the actuator 10, the magnetomotive force is that which tends to produce a magnetic field. The magnetomotive force is most commonly produced by current flowing through a coil of wire and the magnitude of this force is proportional to the current supplied to the coil and the number of turns of the coil. Thus, a unit of magnetomotive force is the ampere turn. In that regard, the data obtained in FIGS. 5–7 is shown in a FIG. 8, which represents a magnetization curve. The curve in FIG. 8 shows the magnetic flux density (flux level) and the magnetomotive force for the three gap sizes indicated in FIGS. 5–7.

Figure 8:
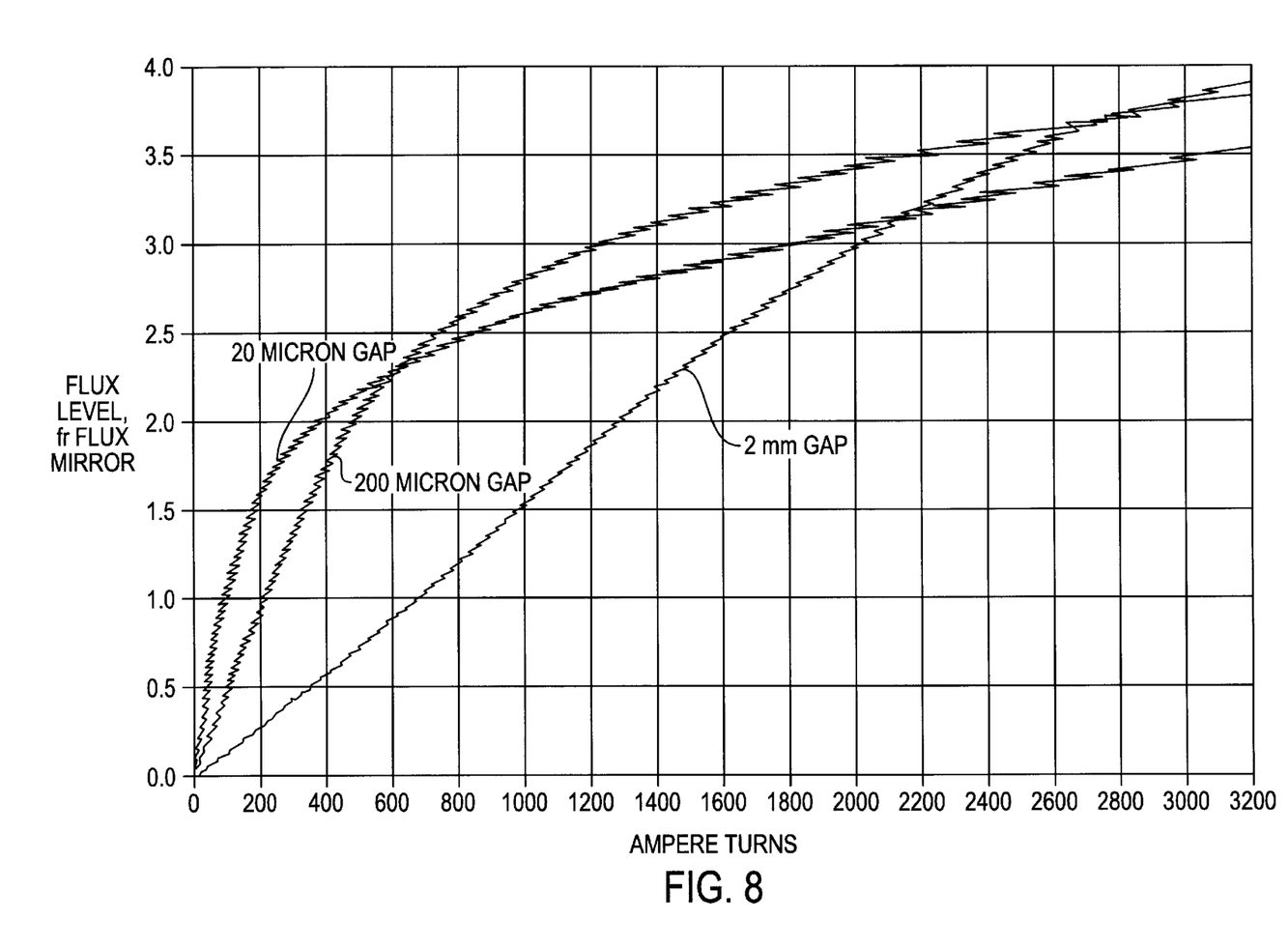
FIG. 8 is a graph of the invention showing flux level vs. ampere turn for air gaps of an actuator of FIG. 1 of 2 mm, 20 microns and 200 microns.

For simplicity of explanation, flux and current were used as the two parameters of the magnetization curve of FIG. 8. As noted above, due to variations of the magnetic characteristics of a ferromagnetic circuit, the amount of flux and therefore, force generated for a given amount of current varies.

Thus, in accordance with the invention, a magnetization curve (FIG. 8) provides the flux level at any point along the curve for a given amount of current in the solenoid 10. The invention provides a means of determining the magnetization curves of solenoids in their finished product state and, if desired, in their final installation and operating condition. The magnetic characteristics are desirable information for the electronic control of solenoids. With the magnetic characteristics known, it is then known approximately what flux density and therefore what force is generated for a given amount of input current. The magnetic characteristic determination can be made with the solenoid in operation to provide immediate controller information update. For an electromagnetic actuator, flux control implementation can use the invention for auto-calibration of the actuator to the controller, in order to correct for variations in magnetic materials, magnetic heat treatment and/or magnetic architecture. With regard to high-speed solenoids of the fuel injector type, the invention can be used for quality control of a finished fuel injector.

Thus, the invention provides difficult to obtain data in a simple and real time output. The specific calibration to a magnetization curve of a solenoid by its control electronics has not been considered to date because it was impractical to implement and the concept of calibration was not an option prior to the invention.

The foregoing preferred embodiments have been shown and described for the purposes of illustrating the structural and functional principles of the present invention, as well as illustrating the methods of employing the preferred embodiments and are subject to change without departing from such principles. Therefore, this invention includes all modifications encompassed within the spirit of the following claims.

What is claimed is:

1. A method of determining magnetic characteristics of an electrically controlled solenoid, the method including:

providing an electronically controlled solenoid having an armature, a stator and a coil operatively associated with said stator, said armature, said stator and said coil defining a magnetic circuit, said armature being spaced from said stator to define an air gap between said armature and said stator;

ramping current to said coil in a generally linear manner over a period of time to define a known current curve, and observing and recording a resulting rate of change of flux in said magnetic circuit at certain points along said current curve so as to determine magnetic characteristics of said solenoid from the resulting rate of change of said flux at said certain points.

2. The method according to claim 1, wherein each rate of change of flux is integrated to determine flux.

3. The method according to claim 1, further comprising:

converting each current of said known current curve to a corresponding ampere turn value; and generating a graph of flux versus ampere turn value.

4. The method according to claim 1, further comprising:

using the known current curve and the resulting rates of change of flux to calibrate the solenoid to a controller of the solenoid.

5. The method according to claim 1, wherein said rate of change of flux is observed by using a flux sensor.

6. The method according to claim 1, wherein said rate of change of flux is observed by measuring a terminal voltage of said coil.

7. The method according to claim 1, wherein said rate of change of flux is observed by using a parametrically determined voltage which mirrors a terminal voltage of said coil.

8. The method according to claim 1, wherein said air gap is fixed at approximately 2 mm.

9. The method according to claim 1, wherein said air gap is fixed at approximately 20 microns.

10. The method according to claim 1, wherein said air gap is fixed at approximately 200 microns.

11. The method according to claim 1, wherein said solenoid is an electromagnetic actuator constructed and arranged to move a fluid exchange valve of an engine.

12. A method of determining magnetic characteristics of an electrically controlled solenoid, the method including:

providing an electronically controlled solenoid having an armature, a stator and a coil operatively associated with said stator, said armature, said stator and said coil defining a magnetic circuit, said armature being spaced from said stator to define a generally constant air gap between said armature and said stator;

ramping flux to said coil in a generally linear manner over a period of time to define a known flux curve, and observing and recording a resulting current in said coil at certain points along said flux curve so as to determine magnetic characteristics of said solenoid from the resulting current at said certain points.

13. The method according to claim 12, further comprising:

converting each value of said resulting current to a corresponding ampere turn value; and generating a graph of flux versus ampere turn value.

14. The method according to claim 12, further comprising:

using the known flux and the resulting current to calibrate the solenoid to a controller of the solenoid.

15. The method according to claim 12, wherein said flux is ramped based on feedback from a flux sensor.

16. The method according to claim 12, wherein said rate of change of flux is ramped based on measuring a terminal voltage of said coil.

17. The method according to claim 12, wherein said rate of change of flux is ramped by using a parametrically determined voltage which mirrors a terminal voltage of said coil.

18. The method according to claim 12, wherein said air gap is fixed at approximately 2 mm.

19. The method according to claim 12, wherein said air gap is fixed at approximately 20 microns.

20. The method according to claim 12, wherein said air gap is fixed at approximately 200 microns.

21. The method according to claim 12, wherein said solenoid is an electromagnetic actuator constructed and arranged to move a gas exchange valve of a vehicle.

22. A method of determining magnetic characteristics of an electrically controlled solenoid, the method including:

providing an electronically controlled solenoid having an armature, a stator and a coil operatively associated with said stator, said armature, said stator and said coil defining a magnetic circuit, said armature being spaced from said stator to define a generally constant air gap between said armature and said stator;

ramping one of current and flux characteristic in the magnetic circuit in a generally linear manner over a period of time to define a known curve, and observing and recording a resulting change in the other of said current and said flux characteristics at certain points along said known curve so as to determine magnetic characteristics of said solenoid from the resulting change at said certain points.

23. The method according to claim 22, wherein said current is ramped and the flux characteristic, defining a rate of change of flux, is observed and recorded.

24. The method according to claim 23, further comprising:

using the known current curve and the resulting flux characteristic to calibrate the actuator to a controller of the actuator.

* * * * *